(12) United States Patent
Lee et al.

(10) Patent No.: US 8,133,220 B2
(45) Date of Patent: *Mar. 13, 2012

(54) ENHANCED ABLATION AND MAPPING CATHETER AND METHOD FOR TREATING ATRIAL FIBRILLATION

(75) Inventors: James K. Lee, Pasadena, CA (US); Martin O'Sullivan, Long Beach, CA (US); Irma Hill, La Verne, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 1135 days.

This patent is subject to a terminal disclaimer.

(21) Appl. No.: 11/654,116

(22) Filed: Jan. 16, 2007

(65) Prior Publication Data
US 2007/0135810 A1 Jun. 14, 2007

Related U.S. Application Data

(63) Continuation of application No. 10/452,103, filed on Jun. 2, 2003, now Pat. No. 7,163,537.

(51) Int. Cl.
*A61B 18/14* (2006.01)
(52) U.S. Cl. .......................................... 606/41; 607/101
(58) Field of Classification Search .................. 606/41, 606/42, 45, 48–50; 607/101–105, 122
See application file for complete search history.

(56) References Cited

U.S. PATENT DOCUMENTS

| RE34,502 E | 1/1994 | Webster, Jr. |
| 5,391,199 A | 2/1995 | Ben-Haim |
| 5,443,489 A | 8/1995 | Ben-Haim |
| 5,462,521 A | 10/1995 | Brucker et al. |
| 5,480,422 A | 1/1996 | Ben-Haim |

(Continued)

FOREIGN PATENT DOCUMENTS
WO  WO 95/02995  2/1995
(Continued)

OTHER PUBLICATIONS

European Search Report completed Oct. 6, 2004, for corresponding Application No. EP 04253132.

(Continued)

*Primary Examiner* — Michael Peffley
(74) *Attorney, Agent, or Firm* — Christie, Parker & Hale, LLP (57) ABSTRACT

A catheter for measuring electrical activity and ablating tissue is provided. The catheter comprises an elongated generally-tubular catheter body. A non-retractable electrode assembly is mounted at the distal end of the catheter body. The electrode assembly comprises a generally tubular ablation electrode formed of a material having shape-memory having a generally straight exposed region and at least one irrigation port in the exposed region through which fluid can pass from the inside to the outside of the ablation electrode. The exposed region is generally transverse to the catheter body. The electrode assembly further comprises a tip at the distal end of the electrode assembly comprising a generally ball-shaped exposed region. First and second distal mapping electrodes are mounted distal to the exposed region of the ablation electrode. At least the first distal mapping electrode, and optionally the second distal mapping electrode, is incorporated into the generally ball-shaped exposed region of the tip. The catheter further comprises an infusion tube extending through the catheter body and having a distal end in fluid communication with the proximal end of the ablation electrode.

26 Claims, 7 Drawing Sheets

U.S. PATENT DOCUMENTS

| | | | |
|---|---|---|---|
| 5,546,951 A | 8/1996 | Ben-Haim | |
| 5,558,091 A | 9/1996 | Acker et al. | |
| 5,568,809 A | 10/1996 | Ben-Haim | |
| 5,643,197 A * | 7/1997 | Brucker et al. | 604/20 |
| 5,800,428 A * | 9/1998 | Nelson et al. | 606/41 |
| 5,891,027 A * | 4/1999 | Tu et al. | 600/374 |
| 5,897,529 A | 4/1999 | Ponzi | |
| 6,120,476 A | 9/2000 | Fung et al. | |
| 6,123,699 A | 9/2000 | Webster, Jr. | |
| 6,171,277 B1 | 1/2001 | Ponzi | |
| 6,183,435 B1 | 2/2001 | Bumbalough et al. | |
| 6,183,463 B1 | 2/2001 | Webster, Jr. | |
| 6,198,974 B1 | 3/2001 | Webster, Jr. | |
| 6,210,407 B1 | 4/2001 | Webster | |
| 6,267,746 B1 | 7/2001 | Bumbalough | |
| 6,371,955 B1 * | 4/2002 | Fuimaono et al. | 606/41 |
| 7,588,568 B2 | 9/2009 | Fuimaono et al. | |
| 2002/0151807 A1 | 10/2002 | Goldin | |

FOREIGN PATENT DOCUMENTS

| | | | |
|---|---|---|---|
| WO | WO 96/05758 | | 2/1996 |
| WO | WO 97/24983 | | 7/1997 |
| WO | WO 98/29033 | | 7/1998 |
| WO | WO 02/47569 | * | 6/2002 |

OTHER PUBLICATIONS

Haissaguerre et al., "Spontaneous Initiation of Atrial Fibrillation by Ectopic Beats Originating in the Pulmonary Veins," *New England Journal of Medicine*, vol. 339, No. 10, pp. 659-666, 1998.

* cited by examiner

ENHANCED ABLATION AND MAPPING CATHETER AND METHOD FOR TREATING ATRIAL FIBRILLATION

CROSS-REFERENCE TO RELATED APPLICATION(S)

This patent application is a continuation of U.S. patent application Ser. No. 10/452,103, filed Jun. 2, 2003 (now U.S. Pat. No. 7,163,537, issued Jan. 16, 2007), and entitled ENHANCED ABLATION AND MAPPING CATHETER AND METHOD FOR TREATING ATRIAL FIBRILLATION, the entire content of which is incorporated herein by reference.

BACKGROUND OF THE INVENTION

Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. It is believed that to treat atrial fibrillation by radio-frequency ablation using a catheter, continuous linear lesions must be formed to segment the heart tissue. By segmenting the heart tissue, no electrical activity can be transmitted from one segment to another. Preferably, the segments are made too small to be able to sustain the fibrillatory process. A preferred technique for treating atrial fibrillation by radio-frequency ablation would be a "branding iron" approach, where a relatively long electrode can be held stationary in good contact with the heart wall while ablation is completed. In this way, a continuous transmural burn may be effected.

U.S. Pat. No. 5,800,428 to Nelson et al. discloses a radio frequency ablation catheter system having a flexible, tubular electrode for creating a continuous linear lesion. The tubular electrode is selectively extendable from the distal end of the catheter. The catheter further comprises mechanisms for remotely manipulating and extending the electrode. However, having an extendable electrode house in the catheter provides less degrees of freedom with respect to the shape, size and length of the tubular electrode. Moreover, the physician has to deal with additional moving and manipulable parts, adding complexity to the procedure. Further, a retractable electrode can cause contamination because blood or coagulate on the electrode can be pulled into and entrapped inside the catheter. The entrapped coagulate can also affect the ability of the electrode to be further extended and retracted. Accordingly, it would be desirable to provide a catheter design having an electrode for creating linear lesions that overcomes these drawbacks.

U.S. patent application Ser. No. 10/199,525, entitled "Atrial Ablation Catheter and Method for Treating Atrial Fibrillation" discloses a catheter having an ablation assembly bent relative to the catheter body and comprising a generally-straight non-retractable tubular electrode formed of a material having shape-memory having at least one irrigation port through which fluid can pass from the inside to the outside of the electrode. Two pairs of ring electrodes are provided, one pair mounted distal to the tubular electrode and one pair mounted proximal to the tubular electrode, for mapping electrical information. All of these components create a relatively long electrode assembly, which can be difficult to maneuver within the tight confines of the atrium. It would therefore be desirable to shorten the length of the ablation assembly while maintaining the functionality.

SUMMARY OF THE INVENTION

The invention is directed to an improved catheter for measuring electrical activity and ablation tissue that has an electrode assembly comprising an elongated ablation electrode and a plurality of mapping electrodes. The mapping electrodes are arranged to minimize the length of the electrode assembly.

In one embodiment, the catheter comprises an elongated generally-tubular catheter body. A non-retractable electrode assembly is mounted at the distal end of the catheter body. The electrode assembly comprises a generally tubular ablation electrode formed of a material having shape-memory having a generally straight exposed region and at least one irrigation port in the exposed region through which fluid can pass from the inside to the outside of the ablation electrode. The exposed region is generally transverse to the catheter body. The electrode assembly further comprises a tip at the distal end of the electrode assembly comprising a generally ball-shaped exposed region. First and second distal mapping electrodes are mounted distal to the exposed region of the ablation electrode. At least the first distal mapping electrode, and optionally the second distal mapping electrode, is incorporated into the generally ball-shaped exposed region of the tip. The catheter further comprises an infusion tube extending through the catheter body and having a distal end in fluid communication with the proximal end of the ablation electrode.

The invention is also directed to methods of using the catheter. In one embodiment, the invention is directed to a method for treating atrial fibrillation comprising inserting the distal end of a catheter as described above into an atria of the heart. Electrical activity within the atria is measured using the distal mapping electrodes, and optionally with proximal mapping electrodes mounted proximal to the exposed region of the ablation electrode. At least one linear lesion is formed in the atrial tissue with the ablation electrode.

In another embodiment, the invention is directed to a method for treating atrial fibrillation comprising providing a catheter as described above and a guiding sheath having proximal and distal ends. The guiding sheath is inserted into the body so that the distal end of the guiding sheath is in an atria of the heart. The catheter is introduced into the proximal end of the guiding sheath and fed through the guiding sheath so that the distal end of the catheter extends out the distal end of the guiding sheath. Electrical activity within the atria is measured using the distal mapping electrodes. At least one linear lesion is formed in the atrial tissue with the tubular electrode.

DESCRIPTION OF THE DRAWINGS

These and other features and advantages of the present invention will be better understood by reference to the following detailed description when considered in conjunction with the accompanying drawings wherein.

DETAILED DESCRIPTION

Figure 1:
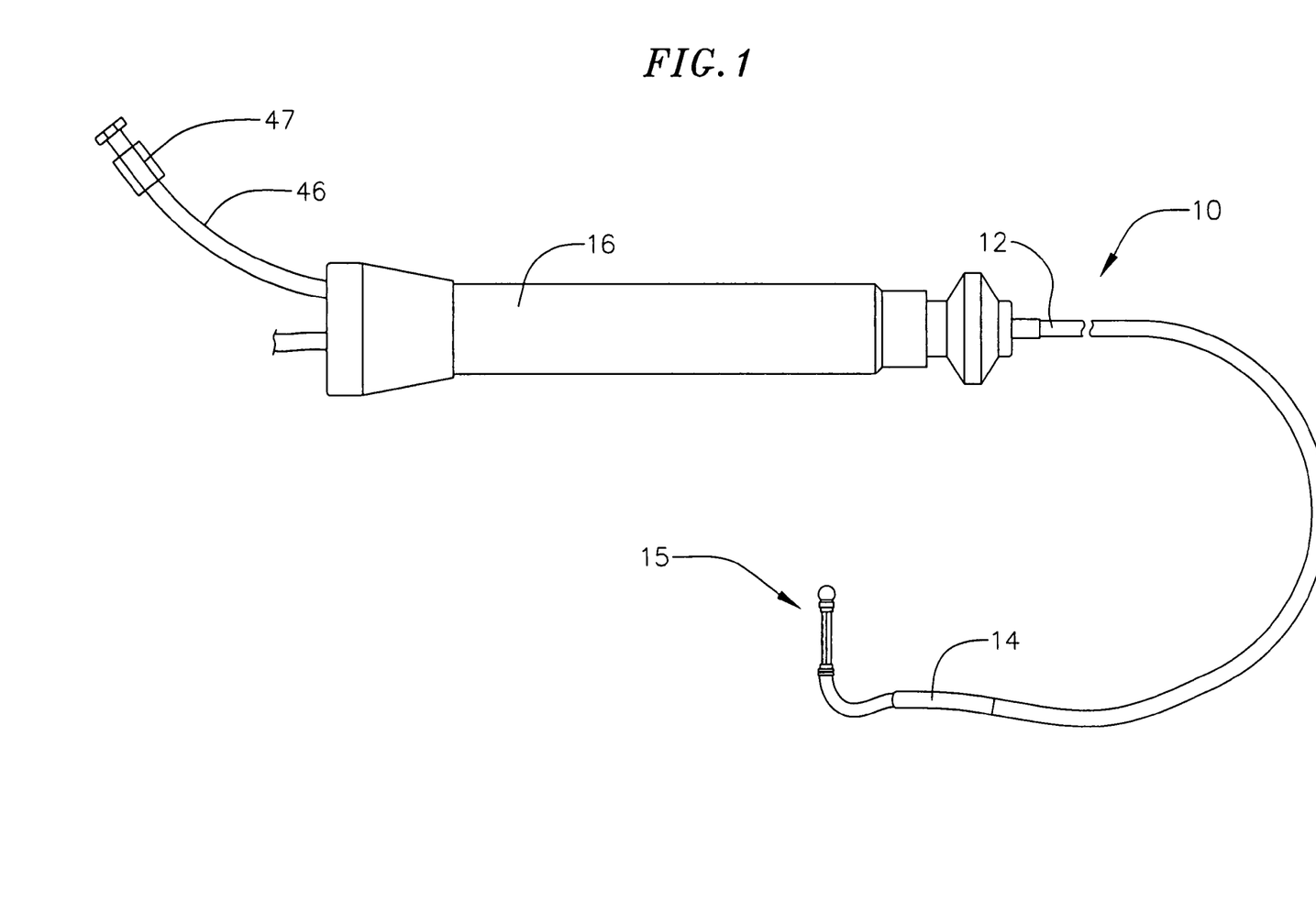
FIG. 1 is a side cross-sectional view of an embodiment of the catheter of the invention.

The invention provides a catheter having an irrigated tubular ablation electrode. As shown in FIG. 1, the catheter comprises an elongated catheter body 10 having proximal and distal ends with an electrode assembly 15 mounted at the distal end of the catheter body and a control handle 16 at the proximal end of the catheter body.

Figure 2:
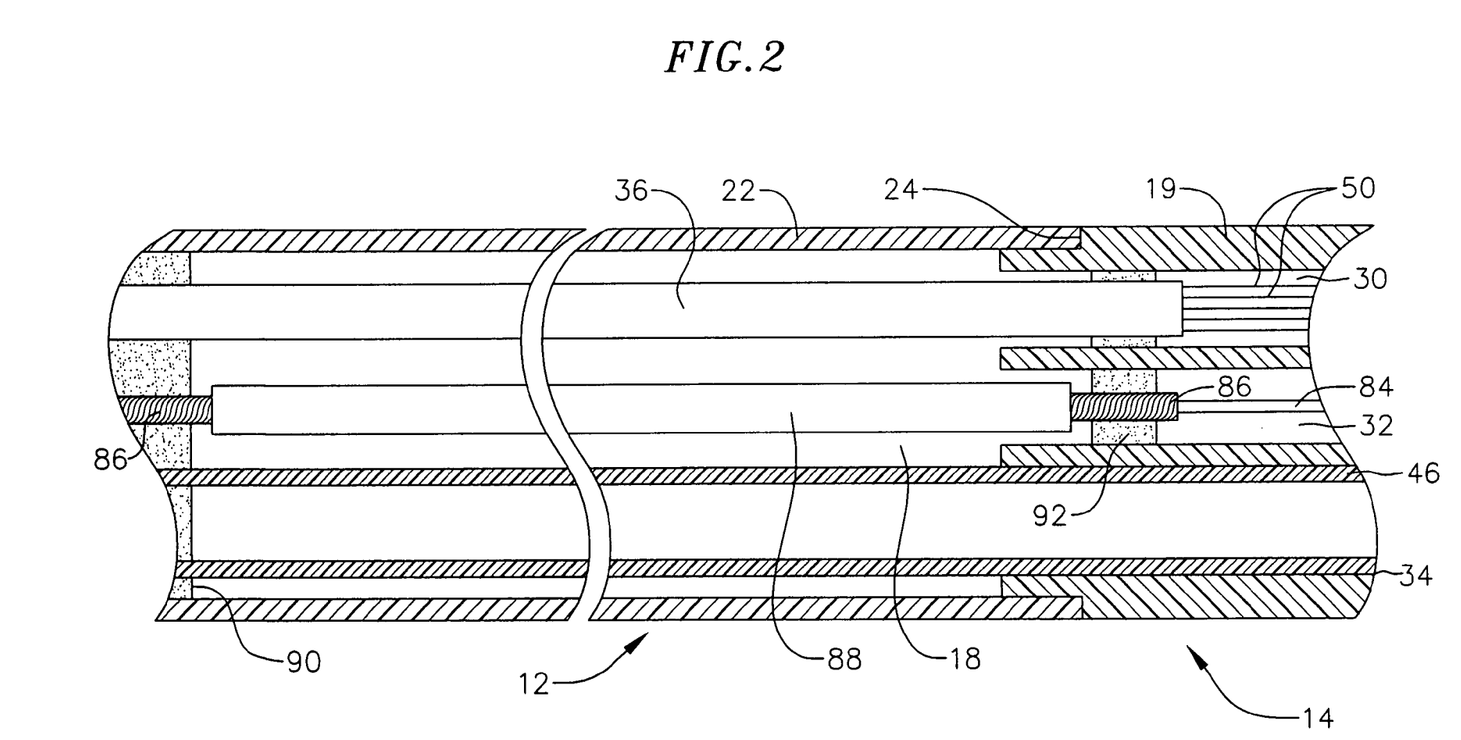
FIG. 2 is a side cross-sectional view of a catheter body according to the invention, including the junction between the catheter body and intermediate section.

With reference to FIG. 2, the catheter body 10 comprises an elongated tubular construction having a relatively long proximal shaft 12 and a relatively short distal shaft 14. The proximal shaft 12 has a single, axial or central lumen 18. The proximal shaft 12 is flexible, i.e., bendable, but substantially non-compressible along its length. The proximal shaft 12 can be of any suitable construction and made of any suitable material. A presently preferred construction comprises an outer wall 22 made of polyurethane or PEBAX. The outer wall 22 comprises an imbedded braided mesh of stainless steel or the like to increase torsional stiffness of the proximal shaft 12 so that, when the control handle 16 is rotated, the distal shaft 14 will rotate in a corresponding manner.

The outer diameter of the proximal shaft 12 is not critical, but is preferably no more than about 8 french, more preferably 7 french. Likewise the thickness of the outer wall 22 is not critical, but is thin enough so that the central lumen 18 can accommodate an infusion tube, a puller wire, lead wires, and any other wires, cables or tubes. If desired, the inner surface of the outer wall 22 is lined with a stiffening tube (not shown) to provide improved torsional stability. In the depicted embodiment, the distal shaft 14 comprises a short section of tubing 19 having three lumens, namely, a lead wire lumen 30, a puller wire lumen 32, and an infusion lumen 34. The wires and tube are described in more detail below. The tubing 19 is made of a suitable non-toxic material that is preferably more flexible than the proximal shaft 12. A presently preferred material for the tubing 19 is braided polyurethane, i.e., polyurethane with an embedded mesh of braided stainless steel or the like, that is more flexible than the catheter body. The number and size of the lumens is not critical and can vary depending on the various wires, tubes and other components carried by the catheter. In a preferred embodiment, the distal shaft 14 has an outer diameter ranging from about 5 french (0.066 inch) to 8 french (0.105 inch), and the lead wire lumen 30 and puller wire lumen 32 are generally about the same size, each having a diameter of from about 0.020 inch to about 0.024 inch, preferably 0.022 inch, with the infusion lumen 34 having a slightly larger diameter of from about 0.032 inch to about 0.038 inch, preferably 0.035 inch.

One means for attaching the proximal shaft 12 to the distal shaft 14 is illustrated in FIG. 2. The proximal end of the distal shaft 14 comprises an outer circumferential notch 24 that receives the inner surface of the outer wall 22 of the proximal shaft 12. The distal shaft 14 and proximal shaft 12 are attached by glue or the like. Other arrangements for the proximal and distal shafts are considered within the scope of the invention. For example, the proximal and distal shafts can be made from a single tubing so that the proximal and distal shafts include the same number of lumens. Alternatively, if a stiffening tube is provided, the stiffening tube can extend slightly beyond the distal end of the proximal shaft 12 (e.g., about 3 mm) and be glued to the proximal shaft, with the proximal end of the distal shaft 14 cored out to receive the distal end of the stiffening tube, creating a lapp joint. The lapp joint and the butt joint formed between the distal end of the proximal shaft 12 and the proximal end of the distal shaft 14 can be secured with polyurethane glue or the like.

If desired, a spacer (not shown) can be located within the proximal shaft 12 at its distal end, adjacent the proximal end of the distal shaft 14. The spacer provides a transition in flexibility at the junction of the proximal shaft and distal shaft, which allows this junction to bend smoothly without folding or kinking. A catheter having such a spacer is described in U.S. Pat. No. 5,964,757, the disclosure of which is incorporated herein by reference.

At the distal end of the distal shaft 14 is a non-retractable electrode assembly 15, as shown in FIGS. 3 to 7. In the depicted embodiment, the electrode assembly 15 has proximal and distal ends and comprises an exposed generally-straight tubular electrode 38 that is generally transverse to the catheter body 12. Two proximal mapping electrodes 40 are mounted proximal to and generally collinear with the tubular electrode's exposed region 38a, and two distal mapping electrodes 41 and 42 are mounted distal to and generally collinear with the tubular electrode.

As used herein, the term "tubular electrode" refers not only to traditional tubular, i.e., cylindrically-shaped, structures having a hollow interior, but also to any other elongated, generally-hollow bodies having, for example, an ovular, square, or other geometrically-shaped cross-sectional area. Other shapes will be apparent to those skilled in the art to achieve the purpose described further herein. Preferably the tubular electrode 38 has an inner diameter ranging from about 0.018 inch to about 0.058 inch and an outer diameter ranging from about 0.020 inch to about 0.060 inch. The length of the tubular electrodes exposed region 38a can vary depending on the desired length of the lesion to be created, and preferably ranges from about 6 mm to about 2 cm, more preferably from about 8 mm to about 12 mm, to create a relatively long lesion.

The tubular electrode 38 is made of a material having shape-memory, i.e., that can be straightened or bent out of its original shape upon exertion of a force and is capable of substantially returning to its original shape upon removal of the force. A particularly preferred material for the tubular electrode is a nickel/titanium alloy. Such alloys typically comprise about 55% nickel and 45% titanium, but may comprise from about 54% to about 57% nickel with the balance being titanium. A preferred nickel/titanium alloy is nitinol, which has excellent shape memory, together with ductility, strength, corrosion resistance, electrical resistivity and temperature stability. A particularly preferred material is nitinol form from 50.8 atomic % nickel, with the balance titanium, having an austenite finish and a transition temperature from about +5° C. to about −25° C., which is commercially available from Nitinol Device Corp. (Fremont, Calif.).

The tubular electrode 38 contains a series of irrigation ports 39 through which fluid can pass during an ablation procedure. Preferably the irrigation ports 39 are located only on the side of the tubular electrode 38 that is to be in contact with the tissue to be ablated, which is typically the side facing away from the catheter body 12. The irrigation ports 39 can be any suitable shape, such as rectangular or ovular slots or round holes. In the embodiment shown in FIGS. 3 and 4, the tubular electrode 38 has six irrigation ports 39, each forming a slot with a length preferably ranging from about 0.018 inch to about 0.020 inch. Preferably the irrigation ports 39 are spaced apart from each other a distance of about 0.125 inch. Having a limited number of irrigation ports 39 on the side of the tubular electrode 38 in contact with the tissue to be ablated allows for more even fluid flow out of the electrode. As would be recognized by one skilled in the art, the precise number, size, shape and arrangement of irrigation ports 39 can vary as desired.

As noted above, the tubular electrode 38 includes an exposed region 38a that is generally transverse to the catheter body 12. Preferably the exposed region 38a forms an angle with the axis of the catheter body 12 ranging from about 75° to about 110°, and the exposed region can be generally perpendicular to the catheter body. In the depicted embodiment, the tubular electrode also includes a non-exposed region 38b at its proximal end, thereby permitting the non-exposed region of the tubular electrode to serve as a shape-defining member for the electrode assembly 15. With this design, the proximal end of the tubular electrode 38 is mounted in the distal end of the distal shaft 14.

Figure 4:
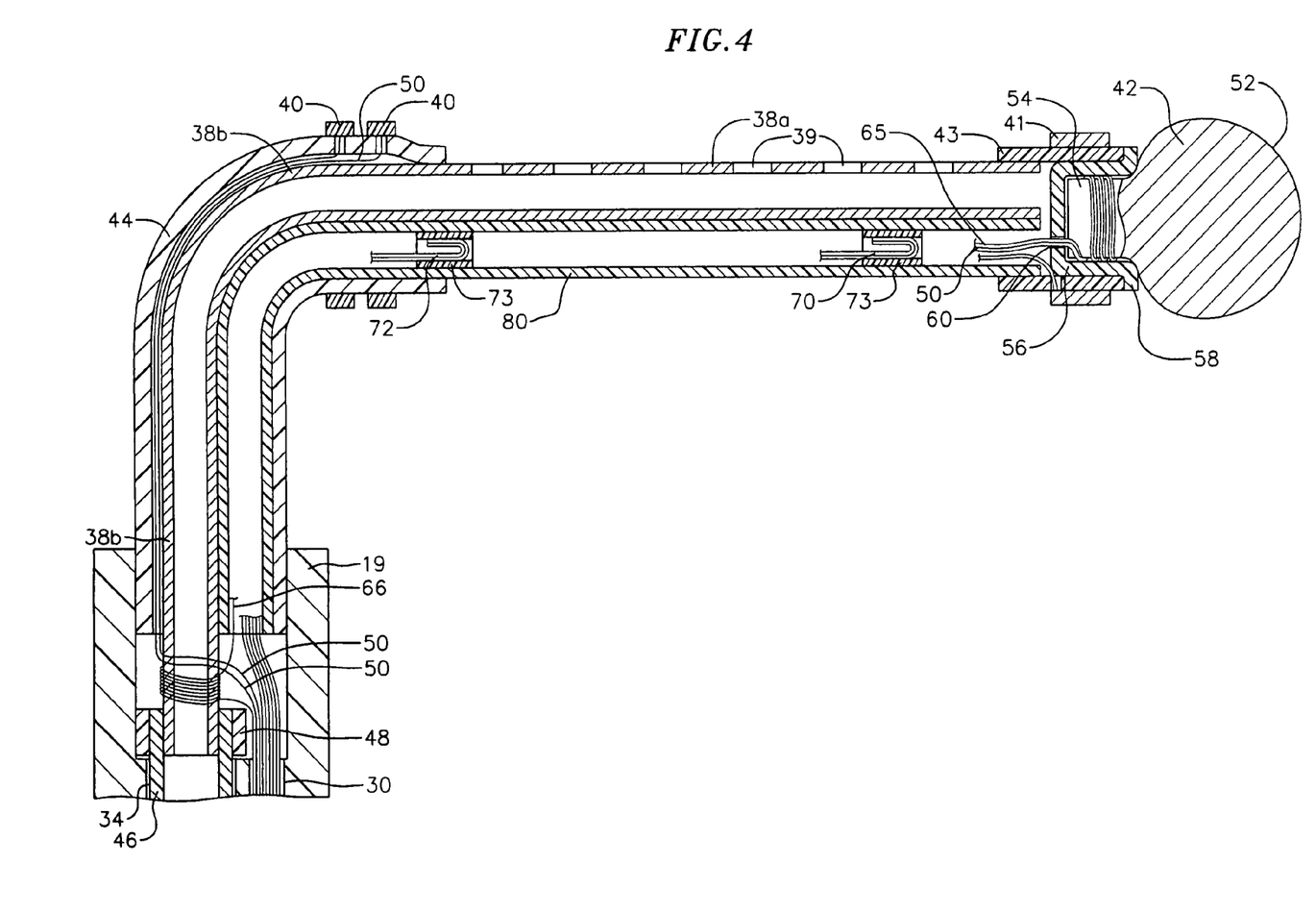
FIG. 4 is a side cross-sectional view of the electrode ablation assembly of FIG. 4 with its proximal end mounted in the distal end of the catheter body.

The tubular electrode's non-exposed region 38b is covered by a non-conductive protective sheath 44, which is preferably made of polyimide, PEBAX or another biocompatible plastic. The proximal end of the protective sheath 44 is mounted in the distal end of the distal shaft 14 and held in place with polyurethane glue or the like, as shown in FIG. 4. Alternatively, the tubular electrode 38 can be shorter, with its proximal end terminating just inside the protective sheath 44.

An infusion tube 46 is provided for infusing fluid, such as saline, into the tubular electrode 38 so that the fluid can pass out through the irrigation ports 39 to cool the tissue being ablated. The infusion tube 46 extends through the infusion lumen 34 of the distal shaft 14, through the proximal shaft 12, out the proximal end of the control handle 16, and terminates in a luer hub 47 or the like at a location proximal to the control handle. In an alternative arrangement, a single lumen side arm (not shown) is fluidly connected to the central lumen 18 near the proximal end of the catheter body 12, as described in more detail in U.S. Pat. No. 6,120,476, the entire disclosure of which is incorporated herein by reference. Alternatively, the infusion tube 46 can terminate within the distal end of the infusion lumen 34 of the distal shaft 14, with a second infusion tube (not shown) provided that extends from the proximal end of the infusion lumen, through the proximal shaft 12 and out through the control handle 16. Such a design is also described in more detail in U.S. Pat. No. 6,120,476.

As shown in FIG. 4, the distal end of the infusion tube 46 extends out the distal end of the infusion lumen 34 and over the proximal end of the tubular electrode 38. The infusion tube 46 is attached to the tubular electrode 38 with polyurethane glue or the like, which also acts to seal the infusion lumen 34 so that fluids cannot pass into or out of the infusion lumen other than through the infusion tube and tubular electrode. A strengthening member 48 comprising a short (e.g., 2 to 5 mm) piece of tubing is provided over the proximal end of infusion tube 46 in which the distal end of the tubular electrode 38 is mounted to enhance the strength of the junction of the infusion tube and tubular electrode.

The two proximal mapping electrodes 40 are mounted on the distal end of the non-conductive protective sheath 44, just proximal to the proximal end of the tubular electrode's exposed region 38a so that they are generally collinear with the exposed region. In the depicted embodiment, each of the two proximal mapping electrodes 40 comprises a ring electrode that is mounted in surrounding relation to the non-conductive protective sheath 44, although other electrode arrangements are considered within the scope of the invention. The ring electrodes can be made of any suitable material, and are preferably made of platinum or platinum and iridium. Each ring electrode can be mounted by any suitable technique, and is preferably mounted by first forming a hole in the non-conductive protective sheath 44. An electrode lead wire 50 is fed through the hole, and the ring electrode is welded in place over the lead wire and non-conductive protective sheath 44.

The two distal mapping electrodes 41 and 42 are mounted just distal to the distal end of the tubular electrode's exposed region 38a so that they are also generally collinear with the exposed region. In one embodiment, the first distal mapping electrode 41, which is closer to the exposed region of the tubular electrode 38 than the second distal mapping electrode 42, is a ring electrode like the proximal mapping electrodes 40 discussed above. The first distal mapping electrode 41 is mounted on a short segment of non-conductive tubing 43 into which the distal end of the tubular electrode 38 extends. The first distal mapping electrode 41 preferably has a length ranging from about 0.5 mm to about 2 mm, more preferably from about 0.5 mm to about 1 mm.

Figure 3:
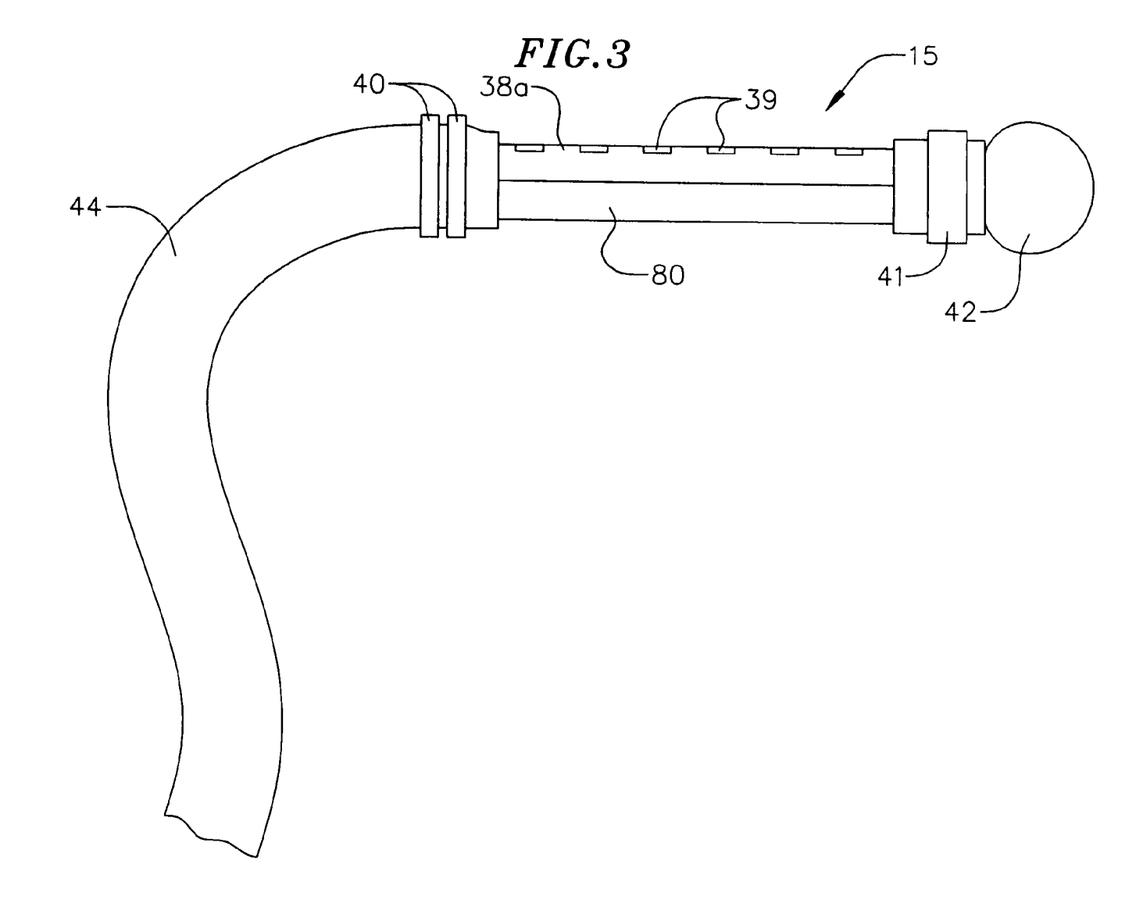
FIG. 3 is a side view of an electrode assembly according to the invention.

As shown in FIGS. 3 and 4, the second distal mapping electrode 42 is in the form of a ball that it mounted at the distal tip of the electrode assembly 15. The ball shape provides a design that is generally more atraumatic than a standard generally-cylindrical tip electrode design. U.S. Pat. No. 6,371,955 discloses a catheter having a non-retractable electrode assembly similar to the present invention and having an atraumatic tip in the form of an elongated covered coil or a generally-short plastic ball, but only one distal mapping electrode. In use, it is desirable to include a second distal mapping electrode for bipolar mapping. However, as discussed above, such an arrangement can be undesirably long. The use of a ball electrode in the present invention advantageously combines the desirable atraumatic design with the desired second distal mapping electrode to thereby reduce the length of the electrode assembly. Typically, the minimum acceptable width for a ring electrode is about 0.5 mm, with the gap between two electrodes of a pair being approximately 0.5 mm. By eliminating one of the distal ring electrodes, the length of the electrode assembly can be reduced by about 1 mm, which can be substantial when maneuvering the electrode assembly within the tight confines of the atrium.

FIG. 4 shows an exemplary construction of the ball-shaped second distal mapping electrode 42. Specifically, the electrode 42 has a generally-spherical distal end 52 with a generally-cylindrical stem 54 extending from the proximal end of the a generally-spherical distal end. The stem 54 has a diameter smaller than that of the generally-spherical distal end 52. The entire electrode 42, i.e., both the generally-spherical distal end 52 and the stem 54 are made of an electrically-conductive material, such as platinum, although the stem and/or a portion of the generally-spherical distal end could be made of a non-conductive material. As used herein, the term "ball-shaped" to describe the second distal mapping electrode is not limited to generally-spherical structures, but includes egg-shaped structures and other elongated structures having a generally-hemispherical distal end.

The stem 54 of the electrode 42 is received by a cup-shaped plug 56 having a rim 58 at its distal end. The proximal end of the plug 56 is mounted in the distal end of the short segment of non-conductive tubing 43 and held in place with polyurethane glue or the like. The proximal end of the plug 56 includes a small opening 60 through which an electrode lead wire 50 can be introduced for electrical connection to the second distal mapping electrode 42. The lead wire 50 can be wrapped around the stem 54 and soldered in place or otherwise attached to the electrode 42 in any other suitable manner.

Preferably the distance between the distal end of the first distal mapping electrode 41 and the proximal end of the second mapping electrode 42 (in the above-described embodiment, the proximal end of the generally-spherical distal end 52) ranges from about 0.5 mm to about 2 mm, more preferably from about 0.5 mm to about 1 mm.

Figure 5:
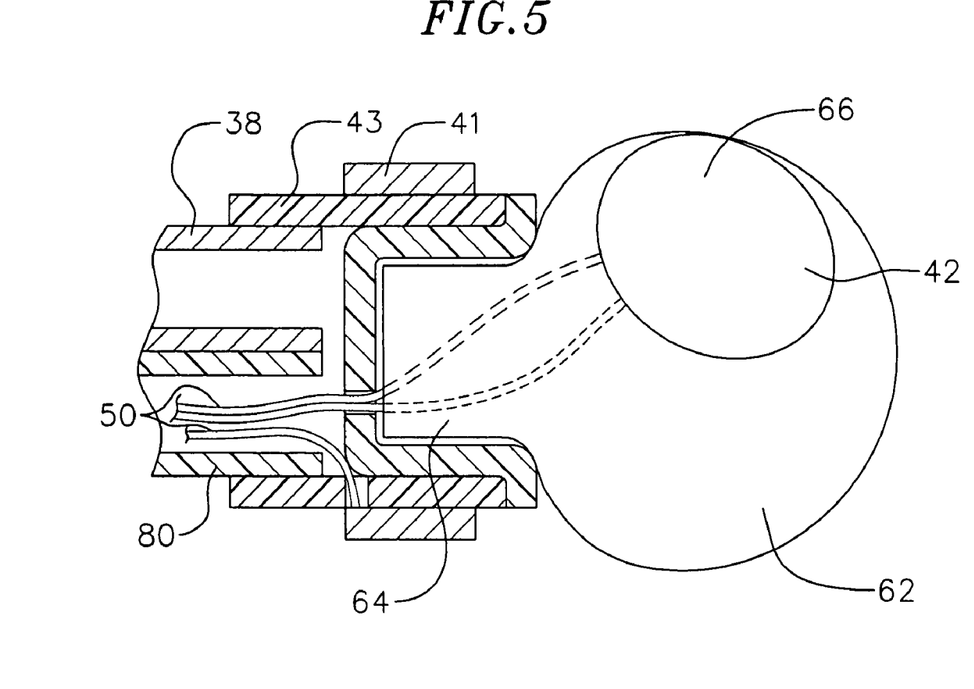
FIG. 5 is a side cross-sectional view of an alternative ball tip for an electrode assembly according to the invention.
Figure 6:
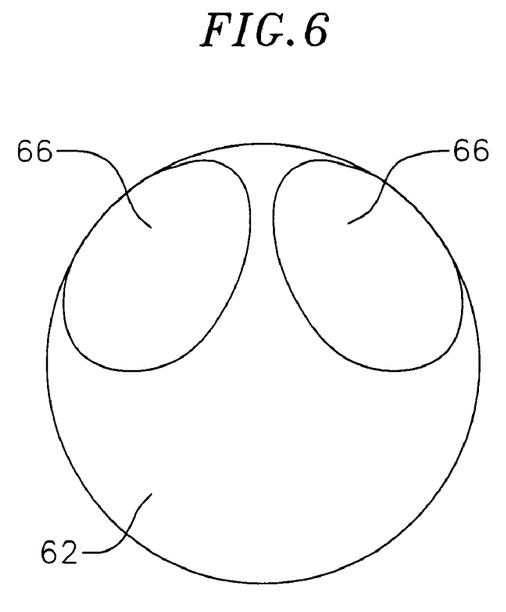
FIG. 6 is an end view of the ball tip of FIG. 5.

FIGS. 5 and 6 show an alternative embodiment where both distal ring mapping electrodes are eliminated and incorporated into a ball tip. This design can reduce the length of the electrode assembly 15 about 2 mm. In this design, a non-conductive ball-shaped tip 62 is provided at the distal end of the non-conductive tubing 43. The non-conductive ball-shaped tip 62 includes a non-conductive stem 64 that is received directly by the non-conductive tubing, but could alternatively be received by a plug as described above. As best shown in FIG. 6, two slightly cup-shaped electrodes 66 are mounted on the outside of the ball-shaped tip 62, preferably both on or near the side of the ball-shaped tip that faces away from the catheter body 12. The cup-shaped electrodes 66 are made of any suitable electrically-conductive material, such as platinum. Two electrode lead wires 50 are soldered or otherwise attached at their distal ends to the two cup-shaped electrodes 66.

To make the ball tip, the entire assembly of the ball-shaped tip 62 on which the cup-shaped electrodes 66 are mounted is covered with a non-conductive covering material (not shown), which can be a cured adhesive, such as polyurethane, or a fused or heat-shrunk plastic, such as pellethane or PEBAX. The non-conductive covering material provides a secure attachment of the separate cup-shaped electrodes 66 to the ball-shaped tip 62. A portion of the non-conductive covering material is then selectively cut, scraped or otherwise removed to expose the two distinct electrode elements 41 and 42.

Figure 7:
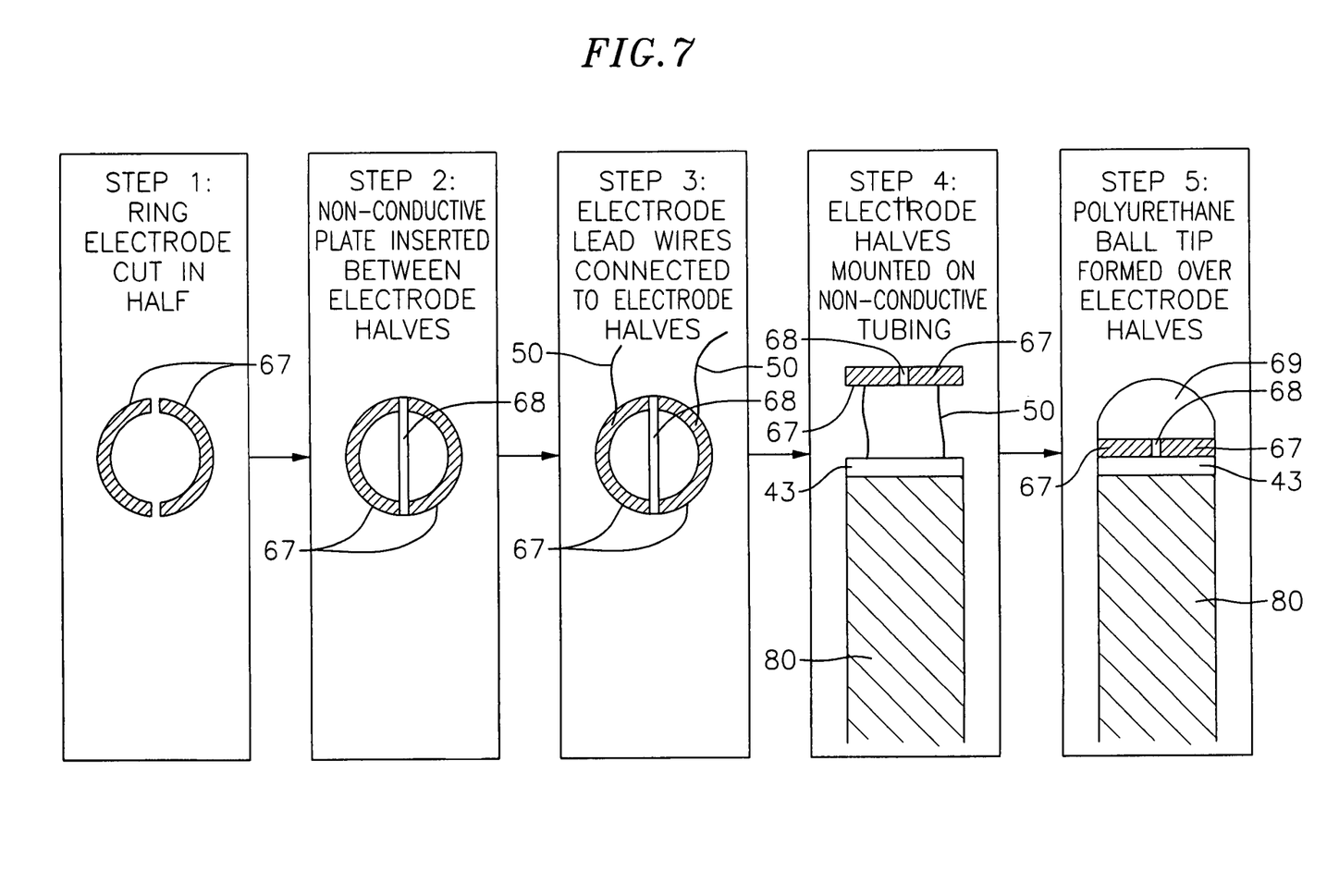
FIG. 7 is a flow chart illustrating a method for making an alternative electrode ball tip for an electrode assembly according to the invention.

The assembly of another alternative design is depicted in FIG. 7. In this design, like the second embodiment described above, both distal mapping electrodes 41 and 42 are incorporated into the ball-shaped tip. With this design, a standard ring electrode is first cut into two electrode halves 67 (Step 1), and a non-conductive plate 68 is inserted between and bonded to the two halves (Step 2). Electrode lead wires 50 are welded at their distal ends to the inside of each electrode half 66 (Step 3). The joined electrode halves 66 are mounted onto the distal end of the short segment of non-conductive tubing 43 with the electrode lead wires inserted through the non-conductive tubing and into the plastic sheath 80 (Step 4). Alternatively, the joined electrode halves can be mounted directly over the tubular electrode 38 and/or protective sheath 80. A drop of polyurethane glue or the like is dropped into the assembly of the electrode halves 67 and non-conductive plate 68 and allowed to cure into a ball tip 69 (Step 5). By this design, the ball tip 69 includes the two ring electrode halves 67, which form the two distal electrodes 41 and 42, with the ring electrode halves forming two generally semi-circular bands being mounted in a generally circular arrangement relative to each other with a non-conductive region between the bands. Preferably the two ring electrode halves 67 are arranged such that they both have a surface facing in the direction of the exposed tubular electrode 38.

An electrode lead wire 50 is also attached to the tubular electrode 38 for electrical connection to a suitable connector (not shown), which is attached to a source of ablation energy, such as RF energy (not shown). In the depicted embodiment, the electrode lead wire 50 is wrapped around the proximal end of the tubular electrode 38 and soldered, welded or otherwise attached to the electrode. The electrode lead wire 50 for the tubular electrode 38 extends through the lead wire lumen 30 of the distal shaft 14, through the central lumen 18 of the proximal shaft 12, and through the control handle 16, and is connected to a suitable source of ablation energy (not shown) by means of an appropriate connector as is generally known in the art.

In the depicted embodiment, a non-conductive protective sheath 80 is provided along the outside of the tubular electrode 38 for carrying the electrode lead wires 50 connected to the distal ring electrodes 41 and 42. The protective sheath 80 extends generally parallel to the tubular electrode 38 and is preferably attached to the tubular electrode along the entire exposed portion 38b of the tubular electrode. The protective sheath 80 is preferably made of polyurethane, polyimide or other suitable biocompatible plastic. In a preferred embodiment, the protective sheath 80 is glued to the tubular electrode 38 with an adhesive such as Krazy Glue® and tied in place using a monofilament or the like. The tubular electrode 38 and protective sheath 80 are then covered with a polyurethane glue or the like, with care being taken not to cover the irrigation ports 39, and the monofilament is removed after the polyurethane glue cures. The proximal end of the protective sheath 80 extends into the non-conductive protective sheath 44 and into the distal shaft 14 where it is glued in place with the proximal end of the tubular electrode 38. Alternatively, the protective sheath 80 can be eliminated and the distal electrode lead wires 50 can extend through the tubular electrode 38, although such wires can adversely affect the flow of irrigation fluid through the tubular electrode.

Additionally, one or more temperature sensing means are provided for the tubular electrode 38. Any conventional temperature sensing means, e.g., a thermocouple or thermistor, may be used. In the depicted embodiment, two thermocouples 70 and 72 are provided. Specifically, a distal thermocouple 70 is provided for measurement distal to the exposed portion of the tubular electrode 38, and a proximal thermocouple 72 is provided for measurement proximal to the exposed portion of the tubular electrode. The distal thermocouple 70 is mounted inside the protective sheath 80 near the distal end of the tubular electrode's exposed region 38a. Similarly, the proximal thermocouple 72 is mounted inside the protective sheath 80 near the proximal end of the tubular electrode's exposed region 38a.

Each thermocouple 70 and 72 is formed by a wire pair. One wire of the wire pair is a copper wire, e.g., a number 38 copper wire, and the other wire of the wire pair is a constantan wire, which gives support and strength to the wire pair. The distal ends of the wires are twisted together and glued within a short piece of plastic tubing 73. The plastic tubing 73 is then glued, wedged or otherwise held in place within the protective sheath 80. The thermocouple wires, along with the electrode lead wires 50, extend through the protective sheath, which as noted above is mounted in the distal end of the distal shaft 14, and then into the lead wire lumen 30 within the distal shaft. As would be recognized by one skilled in the art, other temperature sensing designs can be used, or the temperature sensors can be eliminated altogether.

The placement of the thermocouples in the depicted embodiment is particularly desirable because they are located out of the irrigation zone, i.e., the region in which the irrigation fluid primarily flows from the tubular electrode 38 through the irrigation ports 39. The presence of the fluid can reduce the accuracy of the tissue temperature measurements by the thermocouples. Accordingly, it is desirable to place the thermocouples or other temperature sensing means as close as possible to the tubular electrode 38 while outside the irrigation zone.

All of the electrode lead wires 50 and thermocouple wires 70 and 72 extend through the lead wire lumen 30 in the distal shaft 14. Within the proximal shaft 12, the wires extend through a protective tubing 36 to keep the wires from contacting other components extending through the central lumen 18. The protective tubing 36 is preferably anchored at its distal end to the proximal end of the distal shaft 14 by gluing it in the lead wire lumen 30 with polyurethane glue or the like. The electrode lead wires 50 then extend out through the control handle 16 and to a suitable monitoring device or source of ablation energy (not shown), as appropriate, via a suitable connector (now shown), as is generally known in the art. The thermocouple wires 70 and 72 similarly extend out through the control handle 16 and to a connector (not shown) connectable to a temperature monitor (not shown).

The ball-shaped distal electrode 42 is preferably secured to the distal end of the catheter with a safety wire 65. The distal end of the safety wire 65 is hooked around the stem 54 and glued in place. The safety wire 65 extends through the protective sheath 80 and its proximal end is wrapped around the proximal end of the tubular electrode 38 and optionally soldered, glued or otherwise attached in place. The proximal end of the safety wire 65 can be secured to the catheter in any other suitable manner.

A puller wire 84 is provided for deflection of the distal shaft 14. The puller wire 84 extends through the proximal shaft 12, is anchored at its proximal end to the control handle 16, and is anchored at its distal end to the distal shaft 14. The puller wire 84 is made of any suitable metal, such as stainless steel or Nitinol, and is preferably coated with Teflon® or the like. The coating imparts lubricity to the puller wire 84.

A compression coil 86 is situated within the proximal shaft 12 in surrounding relation to the puller wire 84. The compression coil 86 extends from the proximal end of the proximal shaft 12 to the proximal end of the distal shaft 14. The compression coil 86 is made of any suitable metal, preferably stainless steel. The compression coil 86 is tightly wound on itself to provide flexibility, i.e., bending, but to resist compression. The inner diameter of the compression coil 86 is preferably slightly larger than the diameter of the puller wire 84. The Teflon® coating on the puller wire 84 allows it to slide freely within the compression coil 86. If desired, particularly if the lead wires 50 are not enclosed by a protective tubing 36, the outer surface of the compression coil 86 is covered by a flexible, non-conductive sheath 88, e.g., made of polyimide tubing, to prevent contact between the compression coil and any other wires within the proximal shaft 12.

The compression coil 86 is anchored at its proximal end to the outer wall 22 of the proximal shaft 12 by proximal glue joint 90 and at its distal end to the distal shaft 14 by distal glue joint 92. Both glue joints 90 and 92 preferably comprise polyurethane glue or the like. The glue may be applied by means of a syringe or the like through a hole made between the outer surface of the proximal shaft 12 and the central lumen 18. Such a hole may be formed, for example, by a needle or the like that punctures the outer wall 22 of the proximal shaft 12 that is heated sufficiently to form a permanent hole. The glue is then introduced through the hole to the outer surface of the compression coil 86 and wicks around the outer circumference to form a glue joint about the entire circumference of the compression coil 86.

Figure 8:
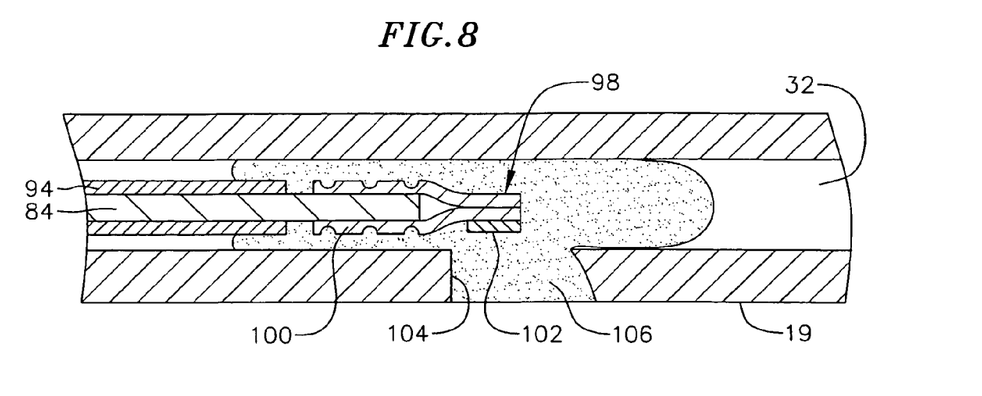
FIG. 8 is a cross sectional view of a portion of the catheter intermediate section showing one means for attaching the puller wire.
Figure 9:
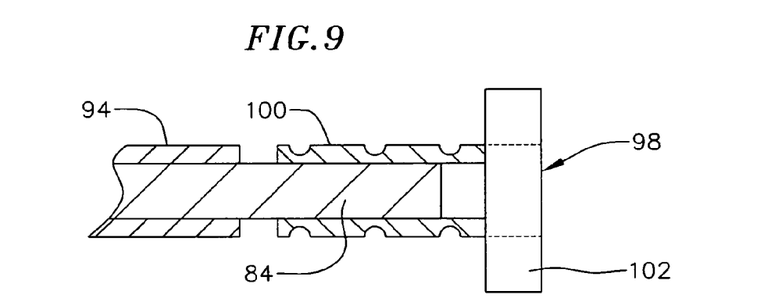
FIG. 9 is a top cross sectional views of a preferred puller wire anchor.
Figure 10:
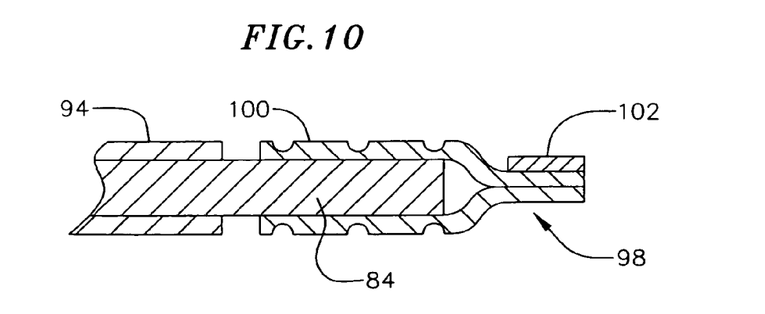
FIG. 10 is a side cross sectional views of the puller wire anchor of FIG. 9.

The puller wire 84 extends into the puller wire lumen 32 of the distal shaft 14. Preferably the puller wire 84 is anchored at its distal end to the side of the shaft 14, as shown in FIGS. 8 to 10. A T-shaped anchor 98 is formed which comprises a short piece of tubular stainless steel 100, e.g., hypodermic stock, which is fitted over the distal end of the puller wire 84 and crimped to fixedly secure it to the puller wire. The distal end of the tubular stainless steel 100 is fixedly attached, e.g., by welding, to a stainless steel cross-piece 102 such as stainless steel ribbon or the like. The cross-piece 102 sits in a notch 104 in a wall of the flexible tubing 19 that extends into the puller wire lumen 32 of the distal shaft 14. The stainless steel cross-piece 102 is larger than the opening and, therefore, cannot be pulled through the opening. The portion of the notch 104 not filled by the cross-piece 102 is filled with glue 106 or the like, preferably a polyurethane glue, which is harder than the material of the flexible tubing 19. Rough edges, if any, of the cross-piece 102 are polished to provide a smooth, continuous surface with the outer surface of the flexible tubing 19. Within the puller wire lumen 32 of the distal shaft 14, the puller wire 84 extends through a plastic, preferably Teflon®, puller wire sheath 94, which prevents the puller wire 84 from cutting into the wall of the distal shaft 14 when the distal shaft is deflected. Any other suitable technique for anchoring the puller wire 84 in the distal shaft 14 can also be used.

Longitudinal movement of the puller wire 84 relative to the proximal shaft 12, which results in deflection of the distal shaft 14, is accomplished by suitable manipulation of the control handle 16. Examples of suitable control handles for use in the present invention are disclosed, for example, in U.S. Pat. Nos. Re 34,502 and 5,897,529, the entire disclosures of which are incorporated herein by reference.

In use, a suitable guiding sheath is inserted into the patient. An example of a suitable guiding sheath for use in connection with the present invention is the Preface™ Braiding Guiding Sheath, commercially available from Biosense Webster (Diamond Bar, Calif.). The distal end of the sheath is guided into one of the atria. A catheter in accordance with the present invention is fed through the guiding sheath until its distal end extends out of the distal end of the guiding sheath. As the catheter is fed through the guiding sheath, the tubular electrode 38 can be straightened to fit through the sheath, and it will return to its original shape upon removal of the sheath.

The proximal and/or distal mapping electrodes are then used to measure electrical activity in the region to be ablated and the generally-tubular ablation electrode is used to form one or more continuous linear lesions by ablation. As used herein, a linear lesion refers to any lesion, whether curved or straight, between two anatomical structures in the heart that is sufficient to block a wavelet, i.e., forms a boundary for the wavelet. Anatomical structures, referred to as "atrial trigger spots", are those regions in the heart having limited or no electrical conductivity and are described in Haissaguerre et al., "Spontaneous Initiation of Atrial Fibrillation by Ectopic Beats Originating in the Pulmonary Veins", New England Journal of Medicine, 339:659-666 (Sep. 3, 1998), the disclosure of which is incorporated herein by reference. The linear lesions typically have a length of from about 1 cm to about 4 cm, but can be longer or shorter as necessary for a particular procedure. The thermocouples or other temperature sensing means can be used to monitor the temperature of the tissue during ablation. The mapping, ablation and temperature measuring steps can be performed in any desired order.

In an alternative embodiment, the electrode assembly further includes a location sensor (not shown) for providing location information about the electrode assembly. Such a design is disclosed in U.S. patent application Ser. No. 10/199,525, entitled "Atrial Ablation Catheter and Method for Treating Atrial Fibrillation," the disclosure of which is incorporated herein by reference. Preferably the location sensor comprises a magnetic-field-responsive coil, as described in U.S. Pat. No. 5,391,199, or a plurality of such coils, as described in International Publication WO 96/05758. The plurality of coils enables six-dimensional position and orientation coordinates to be determined. Alternatively, any suitable position sensor known in the art may be used, such as electrical, magnetic or acoustic sensors. Suitable location sensors for use with the present invention are also described, for example, in U.S. Pat. Nos. 5,558,091, 5,443,489, 5,480,422, 5,546,951, and 5,568,809, and International Publication Nos. WO 95/02995, WO 97/24983, and WO 98/29033, the disclosures of which are incorporated herein by reference.

If desired, two or more puller wires can be provided to enhance the ability to manipulate the intermediate section. In such an embodiment, a second puller wire and a surrounding second compression coil extend through the proximal shaft and into an additional off-axis lumen in the distal shaft. The first puller wire can be anchored proximal to the anchor location of the second puller wire. Suitable designs of catheters having two or more puller wires, including suitable control handles for such embodiments, are described, for example, in U.S. Pat. Nos. 6,123,699, 6,171,277, 6,183,435, 6,183,463, 6,198,974, 6,210,407, and 6,267,746, the disclosures of which are incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter for ablating tissue, the catheter comprising:
    an elongated catheter body having proximal and distal ends and at least one lumen extending therethrough; and
    an electrode assembly mounted at the distal end of the catheter body, the electrode assembly comprising:
        a generally tubular ablation electrode formed of a material having shape-memory and having a generally straight exposed region with proximal and distal ends and at least one irrigation port in the exposed region through which fluid can pass from the inside to the outside of the ablation electrode, the exposed region being generally transverse to the catheter body,
        a tip at a distal end of the electrode assembly and comprising a generally ball-shaped exposed region extending from a distal face of the generally tubular ablation electrode, wherein the generally ball-shaped exposed region has a diameter greater than a diameter of the tubular ablation electrode,
        at least one proximal mapping electrode mounted proximal to and generally collinear with the exposed region of the generally tubular ablation electrode,
        first and second distal mapping electrodes incorporated into the generally ball-shaped exposed region of the tip; and
    means for introducing fluid into the tubular electrode.

2. The catheter according to claim 1, further comprising a distal non-conductive tubing at the distal end of the exposed region of the ablation electrode, the distal non-conductive tubing having proximal and distal ends, wherein the second distal mapping electrode comprises a ring electrode mounted on the distal non-conductive tubing.

3. The catheter according to claim 2, wherein the tip further comprises a stem proximal to the generally ball-shaped exposed region, wherein the stem is mounted in the distal end of the distal non-conductive tubing.

4. The catheter according to claim 1, wherein the generally ball-shaped exposed region of the tip comprises a conductive material.

5. The catheter according to claim 1, wherein the generally ball-shaped exposed region of the tip has an outer surface, wherein at least a portion of the outer surface comprises a conductive material.

6. The catheter according to claim 1, wherein the generally ball-shaped exposed region of the tip has an outer surface, wherein the entire outer surface comprises a conductive material.

7. The catheter according to claim 1, further comprising a distal non-conductive tubing at the distal end of the exposed region of the ablation electrode, the distal non-conductive tubing having proximal and distal ends, wherein the second distal mapping electrode comprises a ring electrode mounted on the distal non-conductive tubing; and
    wherein the generally ball-shaped exposed region of the tip has an outer surface, at least a portion of which comprises a conductive material, the tip further comprising a stem proximal to the generally ball-shaped exposed region, wherein the stem is mounted in the distal end of the distal non-conductive tubing.

8. The catheter according to claim 1, wherein the generally ball-shaped exposed region of the tip has a non-conductive outer surface and the first and second distal mapping electrodes each comprise a generally cup-shaped conductive electrode mounted in surrounding relation to a portion of the non-conductive outer surface of the generally ball-shaped exposed region of the tip.

9. The catheter according to claim 8, further comprising a non-conductive material formed over at least a portion of the non-conductive outer surface of the generally ball-shaped exposed region of the tip such that at least a portion of each of the generally cup-shaped conductive electrodes is not covered by the non-conductive material.

10. The catheter according to claim 1, wherein the first distal mapping electrode comprises a first generally semi-circular band and the second distal mapping electrode comprises a second generally semi-circular band, the first and second generally semi-circular bands being mounted in a generally circular arrangement relative to each other with a non-conductive region between the bands.

11. The catheter according to claim 1, wherein the exposed region forms an angle with the axis of the catheter body ranging from about 75° to about 110°.

12. The catheter according to claim 1, wherein the exposed region is generally perpendicular to the catheter body.

13. The catheter according to claim 1, wherein the electrode assembly further comprises a proximal non-conductive tubing between the distal end of the catheter body and the proximal end of the exposed region of the ablation electrode.

14. The catheter according to claim 13, wherein the at least one proximal mapping electrode is mounted on the proximal non-conductive tubing.

15. The catheter according to claim 1, wherein the at least one proximal mapping electrode comprises a ring electrode.

16. The catheter according to claim 1, wherein the at least one proximal mapping electrode comprises two proximal mapping electrodes.

17. The catheter according to claim 1, further comprising a non-conductive protective tubing extending generally parallel to and along the outside of the exposed region of the ablation electrode.

18. The catheter according to claim 1, wherein the introducing means comprises an infusion tube extending through the catheter body and having proximal and distal ends, wherein the distal end of the infusion tube is in fluid communication with the proximal end of the tubular electrode.

19. The catheter according to claim 1, wherein the tubular electrode comprises nitinol.

20. The catheter according to claim 1, wherein the exposed region of the ablation electrode has a length ranging from about 6 mm to about 2 cm.

21. The catheter according to claim 1, wherein the exposed region of the ablation electrode has a length ranging from about 8 mm to about 12 mm.

22. The catheter according to claim 1, wherein the electrode assembly comprises a proximal temperature sensor mounted near the proximal end of the exposed region of the ablation electrode and a distal temperature sensor mounted near the distal end of the exposed region of the ablation electrode.

23. The catheter according to claim 22, further comprising a non-conductive protective tubing extending generally parallel to and along the outside of the exposed region of the ablation electrode, wherein the proximal and distal temperature sensors are mounted within the protective tubing.

24. The catheter according to claim 1, wherein at least one irrigation port is located only on a side of the exposed region of the tubular electrode that is to be in contact with tissue to be ablated.

25. A method for treating atrial fibrillation comprising:
inserting the distal end of a catheter according to claim 1 into an atria of the heart, measuring electrical activity within the atria using the distal mapping electrodes, and forming at least one linear lesion in the atrial tissue with the ablation electrode.

26. A method for treating atrial fibrillation comprising:
providing a catheter as recited in claim 1 and a guiding sheath having proximal and distal ends;
inserting the guiding sheath into the body so that the distal end of the guiding sheath is in an atria of the heart;
inserting the catheter into the proximal end of the guiding sheath and feeding the catheter through the guiding sheath so that the distal end of the catheter extends out the distal end of the guiding sheath;
measuring electrical activity within the atria using the distal mapping electrodes; and
forming at least one linear lesion in the atrial tissue with the tubular electrode.

* * * * *